United States Patent [19]

Kumar

[11] Patent Number: 5,411,679
[45] Date of Patent: May 2, 1995

[54] BENZOPYRANS
[75] Inventor: Anil Kumar, Pittsburgh, Pa.
[73] Assignee: Transitions Optical, Inc., Pinellas Park, Fla.
[21] Appl. No.: 304,970
[22] Filed: Sep. 13, 1994

Related U.S. Application Data

[63] Continuation of Ser. No. 201,948, Feb. 25, 1994, abandoned, which is a continuation-in-part of Ser. No. 30,932, Mar. 12, 1993, abandoned.
[51] Int. Cl.$^6$ .............. G02B 5/23; C07D 333/50; C07D 311/78
[52] U.S. Cl. .............. 252/586; 549/42; 549/383; 549/457
[58] Field of Search .......... 252/582, 586; 549/42, 549/382, 383, 457

[56] References Cited

U.S. PATENT DOCUMENTS

| | | | |
|---|---|---|---|
| 2,894,003 | 7/1959 | Long et al. | 260/346.2 |
| 2,900,396 | 8/1959 | Harrison | 260/346.1 |
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,720,356 | 1/1988 | Chu | 252/586 |
| 4,816,584 | 3/1989 | Kwak et al. | 544/71 |
| 4,818,096 | 4/1989 | Heller et al. | 252/586 |
| 4,826,977 | 5/1989 | Heller et al. | 252/586 |
| 4,931,221 | 6/1990 | Heller | 252/586 |
| 4,980,089 | 12/1990 | Heller | 252/586 |
| 4,990,287 | 2/1991 | Bennion et al. | 252/586 |
| 5,066,818 | 11/1991 | Van Gemert | 549/389 |
| 5,200,116 | 4/1993 | Heller | 252/586 |
| 5,238,981 | 8/1993 | Knowles | 524/110 |
| 5,244,602 | 9/1993 | Van Gemert | 252/589 |
| 5,274,132 | 12/1993 | Van Gemert | 549/389 |

FOREIGN PATENT DOCUMENTS 562915 9/1993 European Pat. Off. .
816719 8/1937 France .

OTHER PUBLICATIONS

Friedel–Crafts and Related Reactions, George A. Olah, Interscience Publishers, vol. 3, Chap. XXXI, pp. 1–8, 1964.
"Regioselective Friedel-Crafts Acylation of 1,2,3,4-Tetrahydroquinoline and Related Nitrogen Heterocycles", Ishihara, Yugi et al, J. Chem. Soc., Perkin Trans. 1, pp. 3401–3406, 1992.
Heterocyclic Compounds, R. C. Elderfield, 1951, vol. 2, Chapters 3 and 5, pp. 123–144, 164–172.
The Chemistry of Heterocyclic Compounds, H. D. Hartough et al, 1954, vol. 7, Chapter IV, pp. 225–282.
Advances in Heterocyclic Chemistry, A. R. Katritzky et al, 1974, vol. 16, Chapter V.
B. Akermark et al, Acta Chemica Scandinavica, vol. 13, 1959, pp. 1855–1862.
S. Granowitz et al, Acta Pharm. Suec., vol. 15, 1978, pp. 337–360.
J.A.C.S. vol. 61, Apr. 1939, pp. 951–956; Dibenzofuran. IX Metalation of Some Derivatives.
J.A.C.S. vol. 87(2), 1965, pp. 213–217; The ELectron Spin Resonance Spectra of the Dibenzothiophene Radical Anion and its Isologs and the Electronic Structure of Conjugated Sulfur–Containing Heterocycles.
J.A.C.S. vol. 62, Mar. 1940, pp. 667–669. DiBenzofuran. XVIII. Isomeric Metalation Products of Some Phenoils and their Methyl Ethers.

*Primary Examiner*—Philip Tucker
*Attorney, Agent, or Firm*—Frank P. Mallak; Irwin M. Stein

[57] ABSTRACT

Described are novel reversible photochromic benzopyran compounds, examples of which are compounds substituted at the 2 position of the pyran ring and have fused at the benzo portion of the benzopyran a substituted or unsubstituted heterocyclic ring such as a benzothieno or benzofurano group. Also described are organic host materials that contain or that are coated with such compounds. Articles such as ophthalmic lenses or other plastic transparencies that incorporate the novel benzopyran compounds or combinations thereof with complementary photochromic compounds, e.g., spiro(indoline) type compounds, are also described.

22 Claims, No Drawings

BENZOPYRANS

This application is a continuation of application Ser. No. 08/201,948filed Feb. 25, 1994 now abandoned, which is a continuation-in-part of application Ser. No. 08/030,932, filed Mar. 12, 1993 now abandoned.

DESCRIPTION OF THE INVENTION

The present invention relates to certain novel benzopyran compounds. More particularly, this invention relates to novel photochromic benzopyran compounds and to compositions and articles containing such novel benzopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about $-30°$ C. Irradiation of the compounds with visible light or upon raising the temperature to above about $0°$ C. is reported to reverse the coloration to a colorless state.

The present invention relates to novel benzopyran compounds which have been found to have a high activated intensity and a high coloration rate. These compounds are substituted at the 2 position of the pyran ring and have fused at the benzo portion of the benzopyran a substituted or unsubstituted heterocyclic ring such as a benzothieno or benzofurano group.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

Photochromic compounds useful in optical applications, such as conventional ophthalmic lenses, are those which possess (a) a high quantum efficiency for coloring in the near ultraviolet, (b) a low quantum yield for bleaching with white light, and (c) a relatively fast thermal fade at ambient temperature but not so rapid a thermal fade rate that the combination of white light bleaching and thermal fade prevent coloring by the ultraviolet component of strong sunlight. In addition, the aforesaid properties are desirably retained in conventional rigid synthetic plastic materials customarily used for vision correcting ophthalmic and plano lenses when such materials have applied to or incorporated therein such photochromic compounds.

In accordance with the present invention, it has now been discovered that certain novel benzopyran compounds having a high activated intensity and high coloration rate may be prepared. These compounds may be described as benzopyrans substituted at the 2 position of the pyran ring and have a substituted or unsubstituted heterocyclic ring such as a benzothieno or benzofurano group, the 2,3 position or 3,2 position of which are fused to the f, g, or h side of the benzopyran compound and may be represented by the following graphic formula:

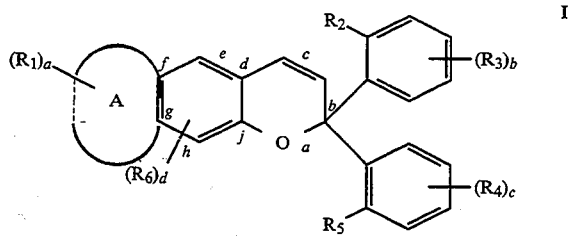

wherein; A may be represented by graphic formulae II A or II B and X is oxygen or sulfur.

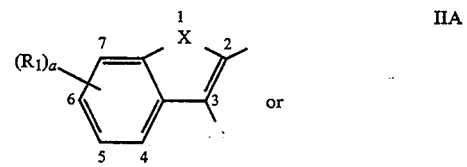

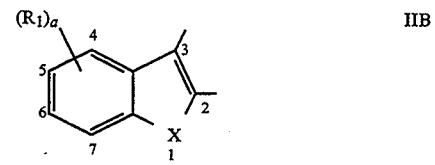

In graphic formula I, A may be the substituted or unsubstituted heterocyclic ring, benzothieno or benzofurano, the 2,3 position or 3,2 position of which are fused to the f, g, or h side of the benzopyran compound of graphic formula I provided that when $R_2$ and $R_5$ are each hydrogen and b and c are 0, A is fused to the g or h side of said benzopyran compound.

Each $R_1$ may be $C_1$–$C_{10}$ alkyl, e.g., methyl, ethyl, propyl, butyl, pentyl, hexyl, heptyl, octyl, nonyl and decyl, $C_5$–$C_7$ cycloalkyl, e.g., cyclopentyl, cyclohexyl, and cycloheptyl, $C_1$–$C_5$ alkylcarbonyl, $C_1$–$C_5$ alkoxycarbonyl, halo($C_1$–$C_5$alkylcarbonyl, $C_1$–$C_5$ monoalkylaminocarbonyl, formyl, hydroxy, halogen, R(R')N—, the group, —O—L, or $R_1$ is a substituted or unsubstituted benzo group fused to the benzo portion of the benzothieno or benzofurano group, said benzo substituents being $C_1$–$C_4$ alkyl, $C_1$–$C_4$ alkoxy, halogen, $C_5$–$C_7$ cycloalkyl, or $C_1$–$C_4$ alkyl substituted $C_5$–$C_7$ cycloalkyl, R is a $C_1$–$C_3$ alkyl, R' is hydrogen or $C_1$–$C_3$ alkyl, L is $C_1$–$C_{10}$ alkyl, phenyl($C_1$–$C_3$)alkyl, e.g., benzyl, phenethyl, phenylpropyl, $C_1$–$C_5$ alkylcarbonyl, $C_1$–$C_5$ alkoxycarbonyl and halo($C_1$–$C_5$)alkyl-carbonyl, which includes mono-, di-, or tri-halo substituents, $C_1$–$C_5$ monoalkylaminocarbonyl, acrylyl, methacrylyl, acetonyl, pyridyl, substituted or unsubstituted arylcarbonyl, said aryl of the arylcarbonyl group being phenyl or naphthyl, said aryl substituents being the same as said benzo substituents, said halogen (or halo) groups being chloro, fluoro, or bromo, and a is the integer 0 or 1. Most preferably, as shown in graphic formulae II A and II B, $R_1$ may be methyl, methoxy, formyl, benzo, methoxycarbonyl, or methylaminocarbonyl.

In graphic formula I, $R_2$ and $R_5$ may each be hydrogen, $C_1$-$C_5$ alkyl, $C_1$-$C_5$ alkoxy, fluoro, or chloro. Most preferably, $R_2$ is hydrogen and $R_5$ is methyl, methoxy, or fluoro. Each $R_3$ and each $R_4$ may be hydroxy, $C_1$-$C_{10}$ alkyl, $C_1$-$C_{10}$ alkoxy, $C_5$-$C_7$ cycloalkyl, halogen, e.g., chloro, fluoro or bromo, R(R')N—, or the group, —O—L', said L' may be phenyl($C_1$-$C_3$) alkyl, acrylyl, or methacrylyl and each b and c may be the integers 0, 1, or 2. Most preferably $R_3$ and $R_4$ are each methyl, methoxy, or fluoro and b and c are the integers 0 or 1. $R_6$ may be $C_1$-$C_{10}$ alkyl, $C_5$-$C_7$ cycloalkyl, $C_1$-$C_5$ alkylcarbonyl, $C_1$-$C_5$ alkoxycarbonyl, halo($C_1$-$C_5$alkylcarbonyl), $C_1$-$C_5$ monoalkylaminocarbonyl, formyl, hydroxy, halogen, e.g., chloro, fluoro or bromo, cyano, R(R')N—, or the group, —O—L, and d is the integer 0 or 1. Most preferably, $R_6$ is methyl, methoxy, formyl, methoxycarbonyl, or methylaminocarbonyl. In the definitions of $R_1$, $R_3$, $R_4$ and $R_6$ in graphic formula I, like letters have the same meaning unless stated otherwise.

Compounds represented by graphic formula V in Reaction A are either purchased or prepared by Friedel-Crafts methods using an appropriately substituted or unsubstituted benzoyl chloride of graphic formula IV with benzene or a commercially available substituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In reaction A, the compounds represented by graphic formulae III and IV are dissolved in a solvent, such as carbon disulfide or methylene chloride, in the presence of a Lewis acid, such as aluminum chloride, to form the corresponding substituted benzophenone represented by graphic formula V.

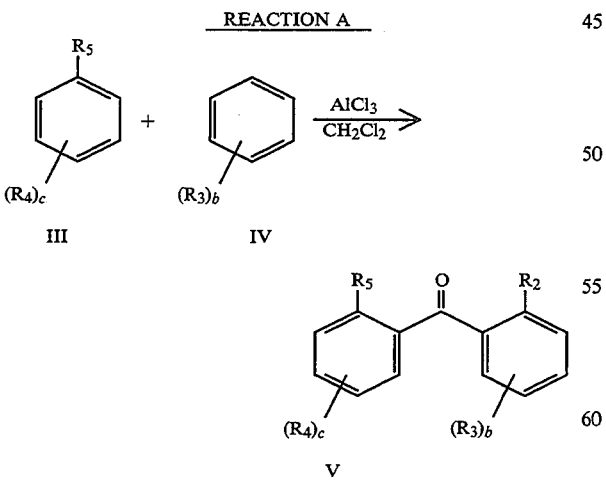

In reaction B, the substituted benzophenone represented by graphic formula V is reacted with sodium acetylide in a suitable solvent, such as dry tetrahydrofuran, to form the corresponding propargyl alcohol represented by graphic formula VI.

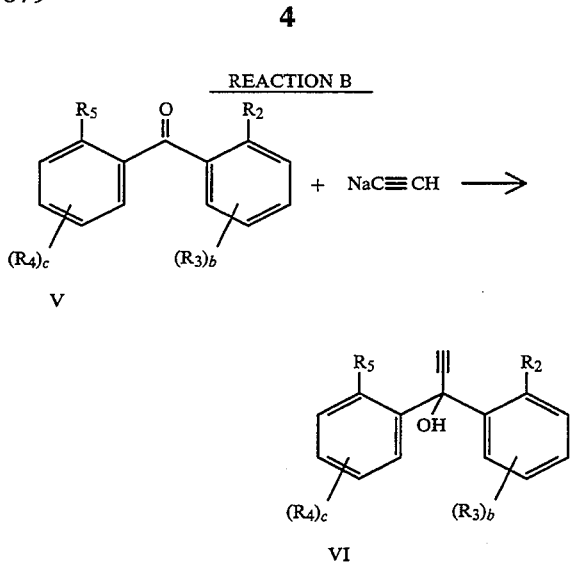

In reaction C, the propargyl alcohol represented by graphic formula VI is coupled with a substituted or unsubstituted hydroxydibenzofuran or hydroxydibenzothiophene, represented by graphic formula VII, under acidic conditions to form the heterocyclic-fused benzopyran of graphic formula I.

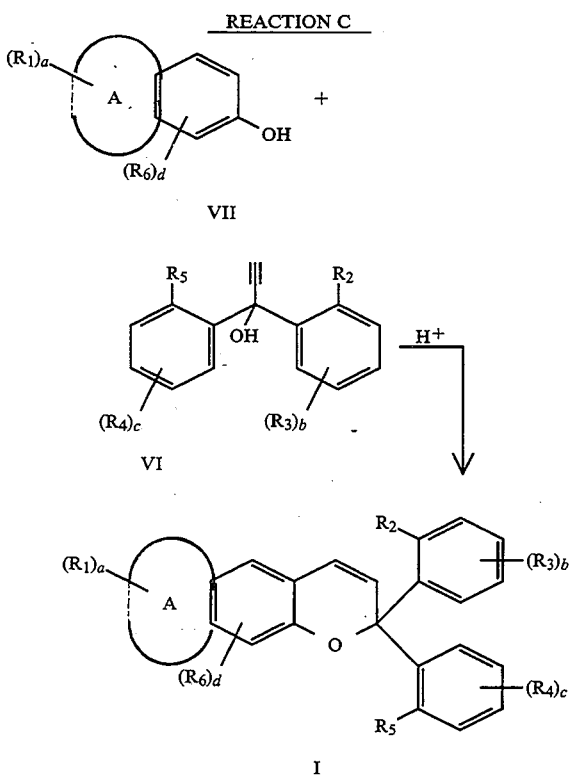

Compounds represented by the graphic formula VII A, when not commercially available, can be prepared by different pathways as shown in Reaction D and described in further detail in the "Journal of the American Chemical Society", Volume 61, 1939, page 951 and Volume 62, 1940, pages 667–669. For example, treatment of compounds represented by graphic formula VIII with 2 equivalents of n-butyl lithium followed by reaction with an electrophile such as, $CO_2$, $(CH_3)_2NCHO$, haloalkane, cyanoalkane, benzonitrile, naphthonitrile, $CH_3ONH_2$, trialkoxyborate, halogen etc. will produce $R_6$ substituents such as —COOH, —CHO, alkyl, alkylcarbonyl, phenylcarbonyl, naphthylcarbonyl, —$NH_2$, —OH, halide, etc.

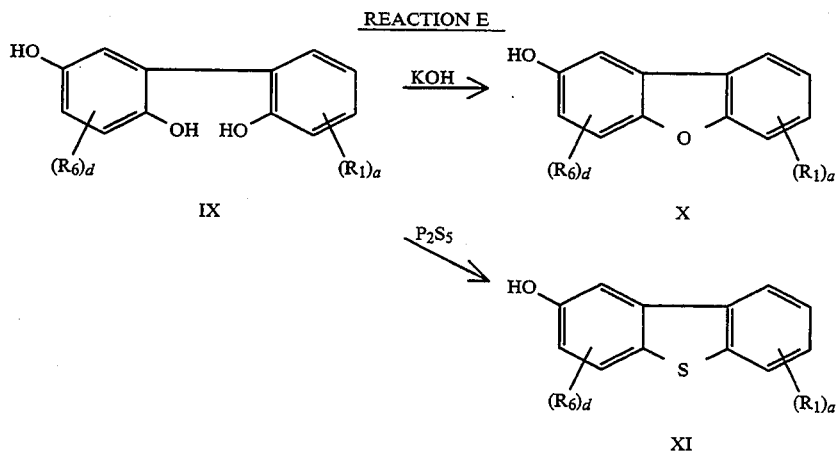

REACTION E

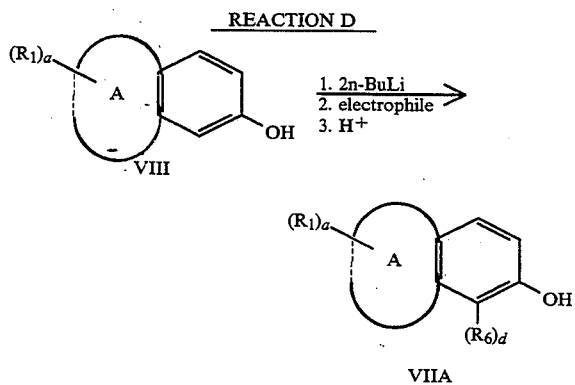

REACTION D

As shown in Reaction E, compounds represented by graphic formulae X and XI, may be prepared from substituted or unsubstituted groups such as 2,2'5 trihydroxybiphenyl represented by graphic formula IX. For further information on this reaction, see the "Journal of the American Chemical Society, Volume 87(2), 1965, page 214.

As shown in Reaction F, the substituted or unsubstituted benzonaphthofuranols, represented by graphic formula XIV, may be prepared by the reaction of a substituted or unsubstituted naphthoquinone, represented by graphic formula XII, with resorcinol, represented by graphic formula XIII. This compound can be further methylated to produce substituted hydroxy benzonaphthofuranols, represented by graphic formula XV. See U.S. Pat. Nos. 2,893,986 and 2,894,003. $R_7$ represents the potential substituents that may be present on the benzene ring fused to the benzothieno or benzofurano groups. Compounds represented by graphic formula XV may be used in place of compounds represented by graphic formula VII in Reaction C to produce naphthofurano fused benzopyrans, i.e., 3-(2,4-dimethoxyphenyl),3-(4-methoxyphenyl)-8-methoxy-(3H)-naphtho[1,2-b]furo[2,3-f]-1-benzopyran, and 3-(2,4-dimethoxyphenyl),3-(4-methoxyphenyl), 3-(4-methoxyphenyl)-(3H)-naphtho[2,1-b]furo[3,2-f]-1-benzopyran.

REACTION F

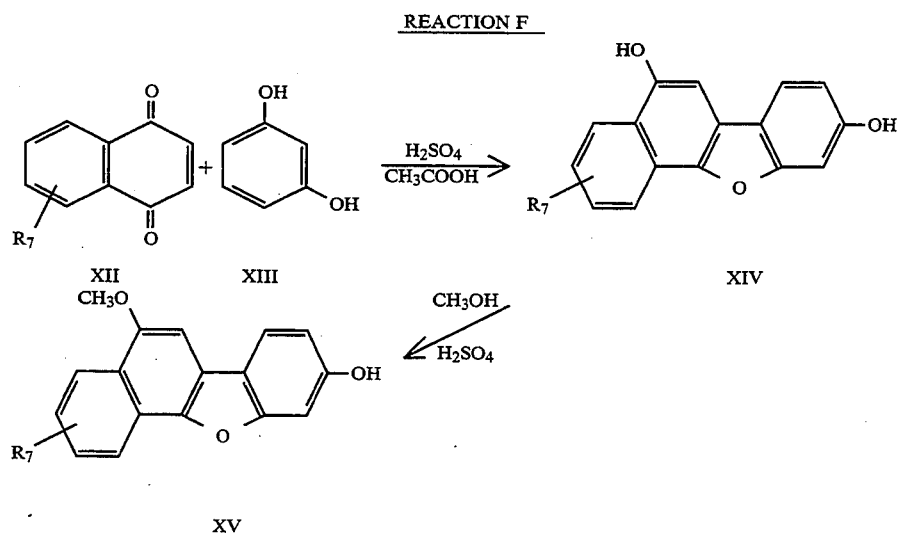

For further information, see *Heterocyclic Compounds*, Robert C. Elderfield, 1951, Vol. 2, Chapter 3 (Dibenzofuran) and Chapter 5 (Dibenzothiaphene); *The Chemistry Of Heterocyclic Compounds*, H. D. Hartough and S.

L. Meisel, 1954, Vol. 7, Chapter IV (Dibenzothiaphene and its Derivatives); *Advances in Heterocyclic Chemistry*, A. R. Katritzky and A. J. Boulton, 1974, Vol. 16, Chapter V (Recent Advances in the Chemistry of Dibenzothiophenes); B. Akermark, H. Erdtman and C. A. Wachtmeister, *Acta ChemiCa Scandinvic*, Vol. 13, 1959, pages 1855-1862; S. Gronowitz, M. Herslof, R. Svenson, G. Bondesson and O. Magnusson, *Acta Pharm. Suec.*, Vol. 15 1978, pages 337-360; and French Patent 816,719 issued Aug. 16, 1937. As described in these references, several different substituents may be attached to the compound of graphic formula VIII by using a combination of reactions.

Compounds represented by graphic formula I may be used in those applications in which organic photochromic substances may be employed, such as optical lenses, e.g., vision correcting ophthalmic and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Benzopyrans represented by graphic formula I exhibit color changes from colorless to colors ranging from yellow-brown to purple-grey.

Examples of contemplated benzopyrans within the scope of the invention are the following:

(1) 3-(2,4-dimethoxyphenyl), 3-(4-methoxyphenyl)-(3H)-benzo(b)furo[2,3-f]-1benzopyran;

(2) 3-(2,4-dimethoxyphenyl), 3-(4-methoxyphenyl)-8-methoxy-(3H)-naphtho[1,2-b]furo[2,3-f]-1-benzopyran;

(3) 2-(2,4-dimethoxyphenyl), 2-(4-methoxyphenyl)-(2H)-benzo(b)thieno[3,2-h]-1-benzopyran;

(4) 2-(2,4-dimethoxyphenyl), 5,8-dimethyl, 2-(4-methoxyphenyl)-(2H)-benzo(b)thieno[3,2-h]-1-benzopyran;

(5) 2-(2,4-dimethoxyphenyl), 2-(4-methoxyphenyl)-(2H)-benzo(b)furo[2,3-h]-1-benzopyran;

(6) 2-(2,4-dimethoxyphenyl), 2-(4-methoxyphenyl)-(2H)-benzo(b)furo[3,2-h]-1-benzopyran;

(7) 2,2-bis(4-methoxyphenyl)-(2H)-benzo(b)-thieno[3,2-h]-1-benzopyran;

(8) 2-(2-fluoro, 4,5-dimethoxyphenyl), 2-(4-methoxyphenyl)-(2H)-benzo(b)thieno[3,2-h]-1-benzopyran;

(9) 3-(2,4-dimethoxyphenyl), 3-(4-methoxyphenyl)-(2H)-benzo(b)furo[2,3-f]-1-benzopyran; and

(10) 3-(2,4-dimethoxyphenyl), 3-(2-fluorophenyl)-(3H)-benzo(b)thieno[2,3-f]-1-benzopyran.

Commercially available photoreactive inorganic glass lenses containing silver halide particles darken to a neutral gray or brown color in sunlight. In order to duplicate this color change in a plastic lens using the organic photochromic 5 benzopyrans of graphic formula I, it is contemplated that such benzopyrans be used individually or in combination with other appropriate complementary organic photochromic materials so that the desired gray or brown color shade is produced when the plastic lens containing such photochromic materials is exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound.

A first group of organic photochromic compounds contemplated for use as complementary photochromic materials are those having an activated absorption maximum within the visible range of greater than 590 nanometers, e.g., between about greater than 590 to 700 nanometers. These materials typically exhibit a blue, blueish-green, or blueish-purple color when exposed to ultraviolet light in an appropriate solvent or matrix. Many of such compounds are described in the open literature. For example spiro(indoline)naphthoxazines have been described, among others, in U.S. Pat. Nos. 3,562,172; 3,578,602; 4,215,010; and 4,342,668. Spiro(indoline)naphthoxazines having certain substituents on the 8' and 9' positions of the naphthoxazine portion of the molecule, such as 1,3,3-trimethyl-5-methoxy-9'-methoxycarbonyl-8'-acetoxy spiro[indoline-2-3'-[3H]naphth-[2,1b]-[1,4]oxazine, are the subject of co-pending U.S. patent application Ser. No. 07/993,587, filed Dec. 21, 1992. Spiro(indoline)pyridobenzoxazines are described in U.S. Pat. No. 4,637,698. Spiro(benzindoline)pyridobenzoxazines and spiro(benzindoline)-naphthoxazines are described in U.S. Pat. No. 4,931,219. Spiro(benzindoline/naphthopyrans are described in Japanese Patent Publication 62/195383. Spiro(indoline)benzoxazines are described in U.S. Pat. No. 4,816,584. Spiro(indoline)benzopyrans, spiro(indoline)naphthopyrans and spiro(indoline)quinopyrans are described, for example, in U.S. Pat. No. 4,880,667. Benzopyrans and naphthopyrans having a nitrogen-containing substituent in the 2-position of the pyran ring are described in U.S. Pat. No. 4,818,096. Spiro(indoline)pyrans are also described in the text, *Techniques in Chemistry*, Volume III, "Photochromism," Chapter 3, Glenn H. Brown, Editor, John Wiley and Sons, Inc., New York, 1971.

A second group of organic photochromic substances contemplated for use as complementary photochromic compounds are those having at least one absorption maximum and preferably two absorption maxima, within the visible range of between about 400 and less than 550 nanometers. These materials typically exhibit a yellow to red/purple color when exposed to ultraviolet light in an appropriate solvent or matrix. Such compounds include certain chromenes, i.e., benzopyrans, 3H-naphtho[2,1-b]-pyrans and 2H-naphtho[1,2-b]-pyrans, many of which are described in the open literature, e.g., U.S. Pat. Nos. 3,567,605; 4,826,977; and 5,066,818. Examples of benzopyrans and naphthopyrans having a spiroadamantane group in the 2-position of the ring are described in U.S. Pat. No. 4,826,977. Naphthopyrans, i.e., 3H-naphtho[2,1-b]-pyrans, having at least one ortho-substituted phenyl substituent at the 3-position of the pyran ring are described in U.S. Pat. No. 5,066,818. Naphthopyran compounds having certain substituents at the number 8 carbon atom and certain substituents at the number 7 or 9 carbon atom, all substituents being on the naphtho portion of the naphthopyran, are the subject of co-pending U.S. patent application Ser. No. 08/080,246, filed Jun. 21, 1993. Naphthopyrans substituted at the 3 position of the pyran ring with (i) an aryl substituent and (ii) a phenyl substituent having a 5- or 6-member heterocyclic ring fused at the number 3 and 4 carbon atoms of the phenyl substituent are the subject of co-pending U.S. patent application Ser. No. 08/080,250 filed Jun. 21, 1993. Naphthopyran compounds substituted at the number 8 carbon atom on the naphtho portion of the naphthopyran ring, with for example, a methoxy group are the subject of U.S. Pat. No. 5,238,931. Naphthopyran compounds, examples of which are 3-aryl-3-arylalkenyl naphthophyrans, are the subject of co-pending U.S. patent application Ser. No. 07/954,630, filed Sep. 30, 1992. Naphthopyrans, i.e., 2H-naphtho[1,2-b]-pyrans, having certain substituents at the number 5 and 6 carbon atoms of the naphtho portion of the naphthopyran and at the 2-position of the pyran ring are the subject of copending U.S. patent application Ser. No. 08/164,187, filed Dec. 9, 1993.

The disclosures of such photochromic compounds in the aforedescribed patents and patent applications are incorporated herein, in toro, by reference. Photochromic articles containing a benzopyran(s) of the present invention may contain also one of the aforesaid complementary photochromic compounds or a mixture of such photochromic compounds, as desired. Mixtures of photochromic compounds may be used to attain certain activated colors, such as a near neutral gray or brown.

The benzopyran compounds of the present invention may be described as a third group of organic photochromic substances having an absorption maximum within the visible range of between about 400 to about 500 nanometers and another absorption maximum within the visible range of between about 500 to about 700 nanometers. These compounds typically exhibit color(s) ranging from yellow/brown to purple/gray when exposed to ultraviolet light in an appropriate solvent or matrix. The organic photochromic substances of the third group may be combined with or used in conjunction with the photochromic substances of the first group that color to purple, blue, e.g., the spiroxazine-type compounds, the second group that color yellow to red/purple, e.g., the pyran-type compounds, or both the first and second groups. Each of the photochromic compounds or substances containing same described herein may be used in amounts and in a ratio such that an organic host material to which the mixture of compounds is applied or in which they are incorporated exhibits a desired resultant color, e.g., a substantially neutral color such as shades of gray or brown, when activated with unfiltered sunlight, i.e., as near a neutral color as possible given the colors of the activated photochromic compounds. The relative amounts of the aforesaid photochromic compounds used will vary and depend in part upon the relative intensities of the color of the activated species of such compounds, and the ultimate color desired. Generally, the weight ratio of the aforedescribed organic photochromic compound combinations, i.e., (first to second), (first to third), and (second to third), will vary from about 1:3 to about 3:1, e.g., between about 0.75:1 and about 2:1. The combination of the first, second, and third organic photochromic compounds may have a weight ratio that will vary from about 1:3:1 to 3:1:3.

A near neutral gray color exhibits a spectrum that has relatively equal absorption in the visible range between 400 and 700 nanometers, e.g., between 440 and 660 nanometers. A near neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr. and Max Saltzman, Second Edition, John Wiley and Sons, N.Y. (1981). As used in the specification, a near neutral color is one in which the chromaticity coordinate values of "x" and "y" for the color are within the following ranges (D65 illuminant): $x=0.260$ to 0.400, $y=0.280$ to 0.400 following activation to 40 percent luminous transmission by exposure to solar radiation (Air Mass 1 or 2).

The amount of each photochromic substance or composition containing same applied to or incorporated into a host material is not critical provided that a sufficient amount is used to produce a photochromic effect discernible to the naked eye. Generally such amount can be described as a photochromic amount. The particular amount used depends often upon the intensity of color desired upon irradiation thereof and upon the method used to incorporate or apply the photochromic substances. Typically, the more compound applied or incorporated, the greater is the color intensity.

Generally, the amount of each photochromic substance incorporated into or applied to the host material may range from about 0.01 or 0.05 to about 10 to 20 percent by weight. More typically, the amount of photochromic substance(s) incorporated into or applied to the host material will range from about 0.01 to about 2 weight percent, more particularly, from about 0.01 to about 1 weight percent, e.g., from about 0.1 or 0.5 to about 1 weight percent, based on the weight of the host material. Expressed differently, the total amount of photochromic substance incorporated into or applied to an optical host material may range from about 0.15 to about 0.35 milligrams per square centimeter of surface to which the photochromic substance(s) is incorporated or applied.

Photochromic compounds of the present invention, mixtures of such compounds with other photochromic compounds, or compositions containing same (hereinafter "photochromic substances") may be applied to or incorporated into a host material by various methods described in the art. Such methods include dissolving or dispersing the substance within the host material, e.g., imbibition of the photochromic substance into the host material by immersion of the host material in a hot solution of the photochromic substance or by thermal transfer; providing the photochromic substance as a separate layer between adjacent layers of the host material, e.g., as a part of a polymer film; and applying the photochromic substance as part of a coating placed on the surface of the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms. See U.S. Pat. No. 5,066,818 column 14, line 41 to column 15, line 25 for examples of the above methods.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material.

Examples of host materials which may be used with the photochromic substances or compositions described herein include: polymers, i.e., homopolymers and copolymers, of polyol(allyl carbonate) monomers, e.g., diethylene glycol bis(allyl carbonate), polymers, i.e., homopolymers and copolymers, of polyfunctional acrylate monomers, polyacrylates, which are polymers of esters of acrylic acid or methacrylic acid, such as methyl acrylate and methyl methacrylate, cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate) copoly(styreneacrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of the transparent polymers are also suitable as host materials. Preferably, the host material is an optically clear polymerized organic material prepared from a polycarbonate resin, such as the carbonate-linked resin derived from bisphenol A and phosgene, i.e., poly(4,4'-dioxydiphenol-2,2-propane), which is sold under the trademark, LEXAN; a poly(methyl methacrylate), such as the material sold under the trademark., PLEXIGLAS; polymerizates of a polyol(allyl carbonate), especially diethylene glycol bis(allyl carbonate), which monomer is sold under the trademark, CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80-90 percent diethylene glycol bis(allyl carbonate) and 10-20 percent vinyl acetate, particularly 80-85 percent of the bis(allyl carbonate) and 15-20 percent vinyl acetate, and copolymers with a polyurethane having terminal diacrylate functionality, as described in U.S. Pat. Nos. 4,360,653 and 4,994,208; and copolymers with aliphatic urethanes, the terminal portions of which contain allyl or acrylyl functional groups as described in U.S. Pat. No. 5,200,485; cellulose acetate, cellulose propionate, cellulose butyrate, cellulose acetate butyrate, polystyrene and copolymers of styrene with methyl methacrylate, vinyl acetate and acrylonitrile.

Polyol (allyl carbonate) monomers which may be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g., glycols. The monomers can be prepared by procedures well known in the art, e.g., U.S. Pat. Nos. 2,370,567 and 2,403,113.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substance is in an inactivated state.

Typically, tinting is accomplished by immersion of the host material in a heated aqueous dispersion of the selected dye. The degree of tint is controlled by the temperature of the dye bath and the length of time the host material is allowed to remain in the bath. Generally, the dye bath is at temperatures of less than 100° C., e.g., from 70° C. to 90° C., such as 80° C., and the host material remains in the bath for less than five (5) minutes, e.g., between about 0.5 and 3 minutes, e.g., about 2 minutes. The degree of tint is such that the resulting article exhibits from about 70 to 85 percent, e.g., 80–82 percent, light transmission.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

The present invention is more particularly described in the following examples which are intended as illustrative only, since numerous modifications and variations therein will be apparent to those skilled in the art.

EXAMPLE 1

Step 1

1,3 dimethoxybenzene (57.0 grams, 0.41 mole) and p-anisoyl chloride (69.0 grams, 0.41 mole) were added to a reaction flask containing 1000 milliliters of methylene chloride. Aluminum chloride (61.0 grams, 0.45 mole) was added slowly and the resulting mixture was stirred for 4 hours under a nitrogen atmosphere. The reaction mixture was added to a 10 weight percent aqueous hydrochloric acid solution containing ice and stirred for about thirty minutes. The organic layer was separated and the aqueous layer was back extracted with 100 milliliters of methylene chloride. The organic portions were combined and washed with water and washed again with a dilute sodium hydroxide solution. The organic layer was dried over magnesium sulfate and the residual methylene chloride was removed under vacuum. The resulting oily product (96.0 grams) solidified upon standing. The solid was crushed, added to hexane, filtered, washed with hexane, and dried. The resulting product, 2,4,4'-trimethoxy-benzophenone was not purified further but used directly in the next step.

Step 2

2,4,4'-trimethoxybenzophenone (15.0 grams, 0.055 mole) from Step 1 and 18.8 grams of a 18 weight percent suspension of sodium acetylide in xylene/mineral oil (0.066 moles of sodium acetylide) were added to a reaction flask containing 300 milliliters of tetrahydrofuran and stirred. After 16 hours at room temperature and under a nitrogen atmosphere, the reaction mixture was dissolved in a 5 weight percent aqueous hydrochloric acid solution. The resulting mixture was extracted with three 50 milliliter portions of diethyl ether. The organic extracts were combined, washed with distilled water, and dried over magnesium sulfate. The solvent, diethyl ether, was removed under vacuum to yield an oily product containing 1-(2,4-dimethoxyphenyl),1-(4-methoxyphenyl)-2-propyn-1-ol, which was not purified further but used directly in the next step.

Step 3

1-(2,4-dimethoxyphenyl), 1-(methoxphenyl)-2-propyn-1-ol (2.0 grams) from Step 2 and 1-hydroxydibenzofuran (1.0 gram, 0.0054 mole) were added to a reaction flask containing 70 milliliters of toluene and stirred at room temperature. A catalytic amount of p-toluenesulfonic acid (about 300 milligrams) was added. The mixture was stirred for 4 hours under a nitrogen atmosphere. Afterwards, the reaction mixture was poured in 50 milliliters of 10 weight percent aqueous sodium hydroxide. The organic layer was separated, washed with distilled water, dried over magnesium sulfate and the remaining toluene was removed under vacuum. The resulting oil was purified using a silica gel column and a 1:1 mixture of hexane:methylene chloride as the eluant. The photochromic fractions were combined and the remaining eluant was removed under vacuum. The oil product, about 1.2 grams, was 98 percent pure, as determined by liquid chromatographic analysis. A nuclear magnetic resonance (NMR) spectrum showed the product to have a structure consistent with 2-(2, 4-dimethoxyphenyl), 2-(4-methoxyphenyl)-(2H)-benzo(b)furo[2, 3-h]-1-benzopyran.

EXAMPLE 2

The procedure of Step 3 of Example 1 was followed except that purchased 1,1 diphenyl-2-propyn-1-ol (1.5 grams, 0.0072 mole) was used in place of 1-(2, 4-dimethoxyphenyl), 1-(4-methoxyphenyl)-2-propyn-1-ol. The recovered product, 0.8 gram, had a melting point of 204°–208° C. A nuclear magnetic resonance (NMR) spectrum showed the desired product to have a structure consistent with 2, 2-diphenyl-(2H)-benzo(b)furo[2,3-h]-1-benzopyran.

EXAMPLE 3

The procedure of Step 3 of Example 1 was utilized except that purchased 2-hydroxydibenzofuran (3.68 grams, 0.02 mole) was used in place of 1-hydroxydibenzofuran and after stirring at room temperature for 4 hours, the mixture was heated to 50° C. and stirred for 1 hour. The recovered product, 0 6.0 grams, had a melting point of 126°–128° C. A nuclear magnetic resonance (NMR) spectrum showed the desired product to have a structure consistent with 3-(2,4-dimethoxyphenyl), 3-(4-methoxyphenyl)-(3H)-benzo(b)furo[3,2-f]-1-benzopyran. A small amount, less than 5 weight percent, of another isomeric product was observed in the NMR spectrum.

EXAMPLE 4

Step 1

The procedure of Step 2 of Example 1 was utilized except that 4,4'-dimethoxybenzophenone (25.0 grams, 0.103 mole) was used in place of 2,4,4'-trimethoxybenzophenone. The recovered product, 32.0 grams, containing 1,1-bis(4-methoxyphenyl)-2-propyn-1-ol was not purified further but used directly in the next step.

Step 2

The procedure of Example 3 was followed except that 1,1-bis(4-methoxyphenyl)-2-propyn-1-ol (4.5 grams) from Step 1 was used in place of 1-(2,4-dimethoxyphenyl), 1-(4-methoxy-phenyl)-2-propyn-1-ol and purchased 2-hydroxydibenzofuran (3.0 grams, 0.016 mole) was used in place of 1-hydroxydibenzofuran. Product yield was 1.8 grams as an oil. A nuclear magnetic resonance (NMR) spectrum showed the desired product to have a structure consistent with a mixture of two isomers of 3, 3-bis(4-methoxyphenyl)-(3H)-benzo(b)furo[3,2-f]-1-benzopyran. A small amount, less than 5 weight percent, of another isomeric product was observed in the NMR spectrum.

EXAMPLE 5

Step 1

Benzoquinone (5.0 grams, 0.046 mole) and 2-naphthol (6.66 grams, 0.046 mole) were added to a reaction flask containing 100 milliliters of acetic acid. Sulfuric acid, 3.0 milliliters of a 50 weight percent aqueous solution, was added to the reaction mixture and the mixture was refluxed for 2 hours. The reaction mixture was cooled to room temperature and poured into water. The resulting precipitate that formed was collected by filtration, washed with water, and dried. The resulting product containing hydroxybenzonaphthofuran was not purified but used directly in the next step.

Step 2

The procedure of Step 3 of Example 1 was followed except that hydroxybenzonaphthofuran (3.0 grams) prepared in Step 1 was used in place of 1-hydroxydibenzofuran. The recovered product, 1.6 grams, had a melting point of 155°–157° C. A nuclear magnetic resonance (NMR) spectrum showed the desired product to have a structure consistent with 3-(2,4-dimethoxyphenyl), 3-(4-methoxyphenyl)-(3H)-naphtho-[2,1-b]-furo[3,2-f]-1-benzopyran. A small amount, less than 5 weight percent, of another isomeric product was observed in the NMR spectrum.

EXAMPLE 6

Step 1

2-Hydroxydibenzofuran (10.0 grams, 0.054 mole) was added to a reaction flask containing about 200 milliliters of tetrahydrofuran under an argon atmosphere and stirred. n-Butyl lithium, 70 milliliters of a 1.6 molar solution, was added dropwise to the flask, and the contents heated to 60° C., and stirred for 14 to 16 hours. The reaction mixture was cooled to room temperature and a solution of dimethylformamide, 4.5 grams in 10 milliliters of diethyl ether, was added dropwise and the reaction mixture was stirred for 48 hours. The reaction mixture was dissolved in 5 weight percent aqueous hydrochloric acid solution. The resulting mixture was extracted with three 50 milliliter portions of diethyl ether. The organic extracts were combined, washed with distilled water, and dried over magnesium sulfate. The solvent, diethyl ether, was removed under vacuum to yield a yellow oily product. The resulting product, 8.0 grams, was crystallized from a 1:1 mixture of diethyl ether:hexane. A nuclear magnetic resonance (NMR) spectrum showed the product to have a structure consistent with 1-formyl, 2-hydroxydibenzofuran.

Step 2

The procedure of Step 3 of Example 1 was followed except that 1-formyl, 2-hydroxydibenzofuran (2.0 grams, 0.0094 mole) prepared above was used in place of 1-hydroxy dibenzofuran. Product yield was 1.8 grams as an oil. A nuclear magnetic resonance (NMR) spectrum showed the desired product to have a structure consistent with 2-(2,4-dimethoxyphenyl), 11-formyl, 2-(4-methoxyphenyl)-(2H)-benzo-(b)furo[2,3-g]-1-benzopyran. A small amount, less than 5 weight percent, of another isomeric product was observed in the NMR spectrum.

EXAMPLE 7

Step 1

The procedure of Step 1 of Example 6 was followed to produce 1-formyl, 2-hydroxydibenzofuran. The procedure of Step 2 of Example 1 was utilized except that 4,4'-dimethoxybenzophenone (5.0 grams, 0.0186 mole) was used in place of 2,4,4'-trimethoxybenzophenone, and the resulting product containing 1,1-bis(4-methoxyphenyl)-2-propyn-1-ol crystallized yielding 5.2 grams of product.

Step 2

The procedure of Step 3 of Example 1 was followed except that 1-formyl, 2-hydroxydibenzofuran (1.0 grams, 0.0047 mole) was used in place of 1-hydroxydibenzofuran and 1,1-bis(4-methoxyphenyl)-2-propyn-1-ol (2.5 grams) from Step 1 was used in place of 1-(2,4-dimethoxyphenyl), 1-(4-methoxyphenyl)-2-propyn-1-ol. Product yield was 0.6 grams as an oil. A nuclear magnetic resonance (NMR) spectrum showed the desired product to have a structure consistent with 2, 2-bis-(4-methoxyphenyl), 11-formyl-(2H)-benzo(b)furo[2,3-g]-1-benzopyran. A small amount, less than 5 weight percent, of another isomeric product was observed in the NMR spectrum.

EXAMPLE 8

Step 1

2-Hydroxydibenzofuran (10.0 grams, 0.054 mole) was added to a reaction flask containing 200 milliliters of diethyl ether under an argon atmosphere and stirred. A 1.6 molar solution of n-butyl lithium (0.123 mole in 77 milliliters hexane) was added dropwise, and the reaction mixture was refluxed for 14 to 16 hours. The reaction mixture was cooled to room temperature and carboxylated by pouring onto dry ice. The solvent, diethyl ether, was removed by distillation and the resulting residue was extracted with a hot (40°–50° C.) solution of 10 weight percent aqueous sodium hydroxide. Carbon dioxide was bubbled through the resulting alkaline solution to precipitate the unreacted 2-hydroxydibenzofuran. The alkaline solution was filtered and the filtrate was washed with diethyl ether two times to remove the remaining phenol. Ten weight percent aqueous hydrochloric acid was added to the resulting solution until the desired product precipitated. The resulting mixture was filtered and the collected solids were washed with diethyl ether. The yield of product, 2-hydroxy-dibenzofuran-1-carboxylic acid, was about 6.5 grams.

Step 2

2-hydroxy-dibenzofuran-1-carboxylic acid (6.5 grams, 0.028 mole) from Step 1, methyl iodide (5.0 grams, 0.035 mole) and sodium bicarbonate (4.0 grams, 0.047 mole) were dissolved in a reaction flask containing 50 milliliters of dimethylformamide and stirred at 60° C. for four hours. The reaction mixture was poured into water and extracted with methylene chloride. The organic layer was separated, washed with water, and dried. Evaporation of the solvent, methylene chloride, resulted in 6.0 grams of an oily product. Analysis by liquid chromatography showed the product to be 95 percent pure. A nuclear magnetic resonance (NMR) spectrum showed the product to have a structure consistent with 1-methoxycarbonyl, 2-hydroxy-dibenzofuran.

Step 3

The procedure of Step 3 of Example 1 was followed except that 1-methoxycarbonyl, 2-hydroxydibenzofuran (2.0 grams, 0.0082 mole) was used in place of 1-hydroxydibenzofuran. Product yield was 1.2 grams as an oil. A nuclear magnetic resonance (NMR) spectrum showed the desired product to have a structure consistent with 2-(2,4-dimethoxyphenyl), 2-(4-methoxyphenyl), 11-methoxycarbonyl-(2H)-benzo(b)furo[2,3-g]-1-benzopyran. A small amount, less than 5 weight percent, of another isomeric product was observed in the NMR spectrum.

EXAMPLE 9

The procedure of Step 3 of Example 1 was followed except that purchased 1,1 diphenyl-2-propyn-1-ol (1.25 grams) was used in place of 1-(2,4-dimethoxyphenyl), 1-(4-methoxyphenyl)-2-propyn-1-ol and purchased 3-hydroxydibenzofuran was used in place of 1-hydroxydibenzofuran. The recovered product, 1.0 gram, had a melting point of 170°–172° C. Analysis by liquid chromatography showed the product to be 98 percent pure. A nuclear magnetic resonance (NMR) spectrum showed the desired product to have a structure consistent with 3,3-diphenyl-(3H)-benzo(b)furo[2,3-f]-1-benzopyran. A small amount, less than 5 weight percent, of another isomeric product was observed in the NMR spectrum.

EXAMPLE 10

Step 1

1,4-naphthoquinone (60.0 grams, 0.375 mole) dissolved in 400 milliliters of acetic acid was added to a reaction flask containing a solution of resorcinol (34.5 grams, 0.313 mole) in acetic acid (150 milliliters) and 50 weight percent sulfuric acid (3.0 milliliters). The mixture was heated to reflux temperature and maintained there for 4 hours. The reaction mixture was cooled to room temperature and poured into water. The precipitate that formed was collected by filtration, washed with water, and dried at 70° C. Analysis by liquid chromatography showed the product to be about 80 percent pure. The product, 5,10-dihydroxybenzo(b)naphtho[2,1-d]furan, was used directly in the next step.

Step 2

5,10-Dihydroxy-benzo(b)]naphtho[2,1-d]furan (60.0 grams, 0.24 mole) was added to a reaction flask containing 300 milliliters of a 1:2 mixture of pyridine and benzene. Acetic anhydride (90 milliliters) was added to the reaction flask and the mixture was heated at reflux temperature for 1 hour. The reaction mixture was cooled to room temperature and filtered. The solids collected by filtration were washed with a 1:1 mixture of benzene and petroleum ether. The solids were air dried and suspended in methanol (300 milliliters) and 200 milliliters of a 20 percent aqueous sodium hydroxide solution was added. The resulting suspension was heated until a clear solution was obtained. The solution was cooled and a solution of 20 weight percent hydrochloric acid (50 milliliters) in 300 milliliters of aqueous ethanol was added. The precipitate that formed was collected by filtration, washed with water, and air dried. Analysis by liquid chromatography showed the product, 5,10-dihydroxy-benzo(b)naphtho[2,1-d]furan, to be about 97 percent pure.

Step 3

5,10-Dihydroxy-benzo(b)naphtho[2,1-d]furan (5.0 grams, 0.02 mole), methanol (10 milliliters) and concentrated sulfuric acid (3 milliliters) were added to a reaction flask and heated to 125° C. for 3 hours. The resulting paste was poured into water (150 milliliters) and 20 milliliters of a 20 weight percent aqueous solution of sodium hydroxide was added. The resulting precipitate was collected by filtration, dissolved in 90° C. water and heated to boiling for 5 minutes. The solution was cooled to room temperature and acetic acid was added until precipitate formed. The precipitate that formed was collected by filtration, washed with water, and air dried. The resulting product, 9-hydroxy, 5-methoxy-benzo(b)naphtho-[2,1-d]furan was found to be 98 percent pure by liquid chromatographic analysis.

Step 4

The procedure of Step 3 of Example 1 was followed except that 9-hydroxy, 5-methoxy-benzo(b)naphtho[2,1-d]furan (2.0 grams, 0.0075 mole) was used in place of 1-hydroxydibenzofuran. Product yield was 0.6 gram as an oil. A nuclear magnetic resonance (NMR) spectrum showed the desired product to have a structure consistent with 3-(2,4-dimethoxyphenyl), 3-(4-methoxyphenyl), 8-methoxy-(3H)-naphtho[1,2-b]furo[2,3-f]-1-benzopyran. A small amount, less than 5 weight percent, of another isomeric product was observed in the NMR spectrum.

EXAMPLE 11

The procedure of Step 3 of Example 1 was followed except that purchased 3-hydroxydibenzothiaphene (1.0 gram, 0.005 mole) was used in place of 1-hydroxydibenzofuran. The recovered product, 0.6 gram, had a melting point of 164°–166° C. A nuclear magnetic resonance (NMR) spectrum showed the desired product to have a structure consistent with 3-(2,4-dimethoxyphenyl), 3-(4-methoxyphenyl)-(3H)-benzo(b)thieno[2,3-f]-1-benzopyran. A small amount, less than 5 weight percent, of another isomeric product was observed in the NMR spectrum. A small amount, less than 5 weight percent, of another isomeric product was observed in the NMR spectrum.

EXAMPLE 12

Step 1

1, 3 dimethoxybenzene (10.0 grams, 0.072 mole) and o-fluorobenzoyl chloride (11.6 grams, 0.072 mole) were added to a reaction flask containing 200 milliliters of methylene chloride and stirred at room temperature. Aluminum chloride (10 grams) was added slowly and the resulting mixture was stirred for 2 hours under a nitrogen atmosphere. The reaction mixture was added to a 10 weight percent aqueous hydrochloric acid solution containing ice and stirred for about thirty minutes. The organic layer was separated and the aqueous layer was back extracted with 100 milliliters of methylene chloride. The organic portions were combined and washed with water and washed again with a dilute sodium hydroxide solution. The organic layer was dried over sodium sulfate and the residual methylene chloride was removed under vacuum. The resulting oily product containing 2-fluoro, 2′, 4′-dimethoxybenzophenone (18.0 grams) was not purified further but used directly in the next step.

Step 2

2,4-Dimethoxy, 2-fluorobenzophenone (5.0 grams) was added to a reaction flask containing 75 milliliters of tetrahydrofuran and stirred at room temperature under a nitrogen atmosphere. A 20 percent molar excess of sodium acetylide supplied as a 18 weight percent suspension in xylene/mineral oil was added and the reaction mixture was stirred for 18 hours. The reaction mixture was added to 10 weight percent aqueous hydrochloric acid and extracted with three 50 milliliter portions of diethyl ether. The organic layer was separated, washed and dried. Evaporation of the solvent, diethyl ether, resulted in an oily residue. The resulting product containing 1-(2,4-dimethoxyphenyl), 1-(2-fluorophenyl)-2-propyn-1-ol (4.0 grams) was not purified further but used directly in the next step.

Step 3

The procedure of Step 3 of Example 1 was followed except that 1-(2,4-dimethoxyphenyl), 1-(2-fluorophenyl)-2-propyn-1-ol (2.3 grams) prepared in Step 2 was used in place of 1-(2,4-dimethoxyphenyl), 1-(methoxyphenyl)-2-propyn1-ol and purchased 3-hydroxydibenzothiaphene (1.0 gram, 0.005 mole) was used in place of 1-hydroxydibenzofuran. The recovered product, 0.6 gram, had a melting point of 176°–178° C. A nuclear magnetic resonance (NMR) spectrum showed the desired product to have a structure consistent with 3-(2,4-dimethoxyphenyl), 3-(2-fluorophenyl-(3H)-benzo(b)thieno[2,3f]-1-benzopyran. A small amount, less than 5 weight percent, of another isomeric product was observed in the NMR spectrum.

EXAMPLE 13

Step 1

Dibenzofuran (16.8 grams, 0.1, mole) was added to a reaction flask containing 200 milliliters of diethyl ether. A solution containing n-butyl lithium (0.21 mole) was added and the reaction mixture was refluxed for 18 hours under a nitrogen atmosphere. n-Butyl magnesium bromide (0.1 mole) was added to the reaction mixture and the mixture was cooled to 0° C. Oxygen gas was blown over the surface of the cold, stirring reaction mixture for 3 hours. A solution of dilute hydrochloric acid and ice was added and the reaction mixture was extracted with three 50 milliliter portions of diethyl ether. The combined diethyl ether extracts were washed with 10 weight percent aqueous sodium hydroxide. The resulting sodium hydroxide solution was acidified with hydrochloric acid yielding an oily product which solidified upon standing. The solid containing solution was filtered and the recovered solid was air dried. The resulting product, 4-hydroxydibenzofuran (11.0 grams), was found to be 95 percent pure by liquid chromatographic analysis and was not purified further but used directly in the next step.

Step 2

The procedure of Step 3 of Example 1 was utilized except that purchased 1,1 diphenyl-2-propyn-1-ol (4.0 grams, 0.019 mole) was used in place of 1-(2,4-dimethoxyphenyl), 1-(4-methoxyphenyl)-2-propyn-1-ol; 4-hydroxydibenzofuran (2.0 grams, 0.011 mole) prepared above was used in place of 1-hydroxydibenzofuran; and the reaction mixture was stirred at room temperature for 2 hours and then stirred for 2 hours at 50° C. instead of stirring for 4 hours at room temperature. Product yield was 0.6 grams as an oil. A nuclear magnetic resonance (NMR) spectrum showed the product to have a structure consistent with 2, 2-diphenyl-(2H)-benzo(b-)furo-[3,2-h]-1-benzopyran.

EXAMPLE 14

The procedure of Step 1 of Example 13 was followed to produce 4-hydroxydibenzofuran. The procedure of Step 3 of Example 1 was followed except that 4-hydroxydibenzofuran (2.0 grams) was used in place of 1-hydroxydibenzofuran. The recovered product, 2.0 grams, had a melting point of 155°-157° C. A nuclear magnetic resonance (NMR) spectrum showed the product to have a structure consistent with 2-(2,4-dimethoxyphenyl), 2-(4-methoxyphenyl)-(2H)-benzo(b)furo[3,2-h]-1-benzopyran.

EXAMPLE 15

Step 1

Dibenzothiaphene (10.0 grams, 0.054 mole) was added to a reaction flask containing 100 milliliters of diethyl ether and stirred. n-Butyl lithium, 70 milliliters of a 1.6 molar solution in hexane, was added slowly while stirring. The resulting reaction mixture was refluxed for 18 hours under a nitrogen atmosphere. n-Butyl magnesium bromide (0.05 mole) was added to the reaction mixture and stirred for an hour. Oxygen gas was blown over the surface of the stirring reaction mixture for 2 hours. The reaction mixture was poured into a dilute hydrochloric acid solution and extracted with three 50 milliliter portions of diethyl ether. The combined diethyl ether extracts were washed with 10 weight percent aqueous sodium hydroxide. The sodium hydroxide solution was acidified with hydrochloric acid yielding a precipitate. The precipitate that formed was collected by filtration, washed with water, and air dried. The resulting product, 4-hydroxydibenzothiaphene (5.0 grams), was not purified further but used directly in the next step.

Step 2

The procedure of Step 3 of Example 1 was utilized except that 4-hydroxydibenzothiaphene (2.0 grams, 0.01 mole), prepared in Step 1, was used in place of 1-hydroxydibenzofuran. The recovered product, 1.6 grams, had a melting point of 135°-140° C. The product was found to be 98 percent pure by liquid chromatographic analysis. A nuclear magnetic resonance (NMR) spectrum showed the product to have a structure consistent with 2-(2,4-dimethoxyphenyl), 2-(4-methoxyphenyl)-(2H)-benzo(b)thieno[3,2-h]-1-benzopyran.

EXAMPLE 16

Step 1

The procedure of Step 1 of Example 15 was followed to produce 4-hydroxydibenzothiaphene. The procedure of Step 2 of Example 1 was utilized except that 4,4'-dimethoxybenzophenone (5.0 grams) was used in place of 2,4,4'-trimethoxybenzophenone, and the resulting product, containing 1,1-bis(4-methoxyphenyl)-2-propyn-1-ol, crystallized yielding 5.2 grams of product.

Step 2

The procedure of Step 3 of Example 1 was followed except that 4-hydroxydibenzothiaphene (2.0 grams, 0.01 mole) was used in place of 1-hydroxydibenzofuran and 1,1-bis-(4-methoxyphenyl)-2-propyn-1-ol (3.5 grams, 0.013 mole) was used in place of 1-(2,4-dimethoxyphenyl), 1-(4-methoxyphenyl)-2-propyn-1-ol. The recovered product, 0.6 grams, had a melting point of 187°-190° C. A nuclear magnetic resonance (NMR) spectrum showed the product to have a structure J consistent with 2,2-bis(4-methoxyphenyl)-(2H)-benzo(b)thieno[3,2-h]-1-benzopyran.

EXAMPLE 17

Step 1

The procedure of Step 1 of Example 13 was followed to produce 4-hydroxydibenzofuran. The procedure of Step 2 of Example 1 was utilized except that 4,4'-dimethoxybenzophenone (5.0 grams, 0.020 mole) was used in place of 2,4,4'-trimethoxybenzophenone, and the resulting product, 1,1-bis-(4-methoxyphenyl)-2-propyn-1-ol, crystallized yielding 5.2 grams of product.

Step 2

The procedure of Step 3 of Example 1 was followed except that 4-hydroxydibenzofuran (2.0 grams, 0.0108 mole) was used in place of 1-hydroxydibenzofuran and 1,1-bis(4-methoxyphenyl)-2-propyn-1-ol (3.0 grams, 0.011 mole) was used in place of 1-(2,4-dimethoxyphenyl), 1-(4-methoxphenyl)-2-propyn-1-ol. The recovered product, 1.6 grams, had a melting point of 148°-150° C. A nuclear magnetic resonance (NMR) spectrum showed the product to have a structure consistent with 2,2-di(4-methoxyphenyl)-(2H)-benzo(b)furo[3,2-h]-1-benzopyran.

EXAMPLE 18

Step 1

The procedure of Step 1 of Example i was followed except that 2-methoxy anisole (25.0 grams, 0.181 mole) was used in place of 1,3 dimethoxybenzene and the reaction mixture containing aluminum chloride was stirred for 1 hour at 40° C. under a nitrogen atmosphere. The resulting oily product was crystallized from hexane. The crystalline product, 3, 4,4'-trimethoxybenzophenone (45.0 grams), was not purified further but used directly in the next step.

Step 2

The procedure of Step 2 of Example 1 was utilized except that 3, 4,4'-trimethoxybenzophenone (20.0 grams, 0.073 mole) was used in place of 2,4,4'-trimethoxybenzophenone. The solvent, diethyl ether, was removed under vacuum to yield an oily product, 1-(3,4-dimethoxyphenyl), 1-(methoxphenyl)-2-propyn-1-ol, which was not purified further but used directly in the next step.

Step 3

The procedure of Step 1 of Example 15 was followed to produce 4-hydroxydibenzothiaphene. The procedure of Step 3 of Example 1 was followed except that 4-hydroxydibenzothiaphene (2 grams, 0.01 mole) was used in place of 1-hydroxydibenzofuran and 1-(3,4-dimethoxyphenyl), 1-(4-methoxyphenyl)-2-propyn-1-ol (3.0 grams, 0.01 mole) was used in place of 1-(2,4-dimethoxyphenyl), 1-(4-methoxyphenyl)-2-propyn-1-ol. Product yield was 0.6 gram as an oil. A nuclear magnetic resonance (NMR) spectrum showed he product to have a structure consistent with 2-(3,4-dimethoxyphenyl), 3-(4-methoxyphenyl)-(2H)-benzo(b)thieno[3,2-h]-1-benzopyran.

EXAMPLE 19

The procedures of Step 1 and 2 of Example 12 were used to produce 1-(2-fluorophenyl), 1-(methoxphenyl)-2-propyn-1-ol. The procedure of Step 3 of Example 1 was followed except that 4-hydroxydibenzothiaphene (2.0 grams, 0.01 mole) was used in place of 1-hydroxydibenzofuran and 1-(2-fluorophenyl), 1-(4-methoxphenyl)-2-propyn-1-ol (3.5 grams, 0.013 mole) was used in place of 1-(2,4-dimethoxyphenyl), 1-(4-methoxyphenyl)-2-propyn-1-ol. Product yield was 1.6 gram as an oil. A nuclear magnetic resonance (NMR) spectrum showed the product to have a structure consistent with 2-(2-fluorophenyl), 2-(4-methoxyphenyl)-(2H)-benzo(b)thieno[3,2-h]-1-benzopyran.

EXAMPLE 20

Step 1

Bromine (11 milliliters, 0.016 mole) was added to a reaction flask containing dibenzothiaphene (10.0 grams, 0.053 mole) in 17 milliliters of carbon disulfide over a period of 10 minutes. The mixture was stirred at room temperature for 1 hour. The precipitate that formed was collected by filtration, washed with ethanol, and dried. Liquid chromatographic analysis revealed that the product, 2,8-dibromodibenzothiaphene, was 98 percent pure.

Step 2

2,8-Dibromodibenzothiaphene (10.0 grams, 0.029 mole) was added to a reaction flask containing 150 milliliters of diethyl ether and stirred at 0° C. under an argon atmosphere. A solution of n-butyl lithium (0.06 molar) was added dropwise and the reaction mixture was stirred at 5° C. for 1 hour followed by stirring at room temperature for one hour. The reaction mixture was cooled to 0° C. and dimethyl sulfate (0.06 mole) was added dropwise. The reaction mixture was added to water and the mixture was extracted with diethyl ether. The resulting organic layer was separated, and dried over sodium sulfate. Evaporation of the solvent, diethyl ether, left an oily product. Column chromatography using hexane as the eluant was employed to purify the product. Liquid chromatographic analysis revealed that the resulting product, 2,8-dimethyldibenzothiaphene (5.0 grams) was 92 percent pure.

Step 3

2,8-Dimethyldibenzothiaphene (3.0 grams, 0.014 mole) was added to a reaction flask containing 100 milliliters of diethyl ether. n-Butyl lithium (0.028 mole), contained in 18 milliliters of a 1.6 molar solution in hexane, was added to the solution and the reaction mixture was refluxed for 16 hours. The reaction was cooled to 10° C. and n-butyl magnesium bromide (0.014 mole) contained in 7 milliliters of a 2.0 molar solution, was added dropwise while maintaining the temperature of 10° C. The reaction mixture was stirred for 2 hours and oxygen gas was blown over the surface of the stirring reaction mixture for 5 hours. A solution of dilute hydrochloric acid and ice was added and the reaction mixture was extracted with three 50 milliliter portions of diethyl ether. The combined diethyl ether extracts were washed with a 10 weight percent aqueous sodium hydroxide. The resulting sodium hydroxide solution was acidified with hydrochloric acid yielding a precipitate which was collected by filtration. The precipitate was air dried yielding 1.5 grams of the desired product, 2,8-dimethyl, 4-hydroxydibenzothiaphene, which was used in the next step without further purification.

Step 4

2,8-Dimethyl, 4-hydroxydibenzothiaphene (1.5 grams, 0 0.0065 mole), 1-(2,4-dimethoxyphenyl), 1-(methoxphenyl)-2-propyn-1-ol (2.0 grams, 0.0067 mole), and 100 milligrams of p-toluene sulfonic acid were dissolved in 70 milliliters of toluene and stirred at room temperature for 4 hours. p-Toluene sulfonic acid (150 milligrams) was added to the reaction mixture and stirred another hour. A 10 weight percent aqueous solution of sodium hydroxide was added to the reaction mixture to quench the reaction. The reaction mixture was extracted with toluene. The organic layer was separated, dried, and concentrated by evaporation of the solvent, toluene. The resulting dark brown oil was purified by column chromatography using a mixture of 1:1 chloroform:hexane as the eluant. The recovered product, 0.8 gram, had a melting point of 110°–112° C. A nuclear magnetic resonance (NMR) spectrum showed the product to have a structure consistent with 2-(2,4-dimethoxyphenyl), 5,8-dimethyl, 2-(4-methoxyphenyl)-(2H)-benzo(b)thieno-[3,2-h]-1-benzopyran.

EXAMPLE 21

Step 1

The procedure of Step 1 of Example 1 was followed except that 4-fluoro-2-methoxyanisole (25.0 grams, 0.181 mole) was used in place of 1,3dimethoxybenzene and the reaction mixture containing aluminum chloride was stirred for 1 hour at 40° C. under a nitrogen atmosphere. The resulting oily product was crystallized from hexane. The crystalline product, 2-fluoro-4,5,4'-trimethoxybenzophenone (45.0 grams), was not purified further but used directly in the next step.

Step 2

The procedure of Step 2 of Example 1 was utilized except that 2-fluoro-4,5,4'-trimethoxybenzophenone, (5.0 grams, 0.017 mole) was used in place of 2,4,4'-trimethoxybenzophenone. The solvent, diethyl ether, was removed under vacuum to yield an oily product containing 1-(2-fluoro, 4,5-dimethoxyphenyl), 1-(4-methoxphenyl)-2-propyn-1-ol, which was not purified further but used directly in the next step.

Step 3

The procedure of Step 1 of Example 15 was followed to produce 4-hydroxydibenzothiaphene. The procedure of Step 3 of Example 1 was followed except that 4-hydroxydibenzothiaphene (1.5 grams, 0.0075 mole) was used in place of 1-hydroxydibenzofuran and 1-(2-fluoro, 4,5-dimethoxyphenyl), 1-(4-methoxyphenyl)-2-propyn-1-ol (2.8 grams), prepared in Step 2, was used in place of 1-(2,4-dimethoxyphenyl), 1-(4-methoxyphenyl)-2-propyn-1-ol. The recovered product, 3.0 grams, had a melting point of 196°–198° C. A nuclear magnetic resonance (NMR) spectrum showed the product to have a structure consistent with 2-(2-fluoro, 4,5-dimethoxyphenyl), 2-(4-methoxyphenyl)-(2H)-benzo(b)-thieno[3,2-h]-1-benzopyran.

Comparative Example

The procedure of Step 3 of Example 1 was followed except that purchased 1,1 diphenyl-2-propyn-1-ol (1.5 grams, 0.0072 mole) was used in place of 1-(2,4-dimethoxyphenyl), 1-(4-methoxyphenyl)-2-propyn-1-ol, and 2-hydroxybenzofuran (1.3 grams, 0.0072 mole) was used in place of 1-hydroxybenzofuran. The recovered product, 1.0 gram, had a melting point of 137°–140° C. A nuclear magnetic resonance (NMR) spectrum showed the product to have a structure consistent with 3,3-diphenyl(3H)-benzo(b)furo[3,2-f]-1-benzopyran.

EXAMPLE 22

Part A

The benzopyrans prepared in the Examples and Comparative Example were incorporated into an ethyl cellulose resin by the following procedure. About 30 milligrams of the photochromic compound was added to 2.0 grams of a 10 weight percent ethyl cellulose solution in toluene. The benzopyran compound was dissolved by warming and stirring on a steam bath. Approximately 2.0 grams of the resultant solution was deposited on the edge of a 75 by 25 millimeter (mm) glass slide. Using a draw down bar, a 0.2 mm layer of photochromic resin solution was placed evenly on the slide and permitted to dry.

Part B

The photochromic test samples prepared in Part A were tested for photochromic response rates on an optical bench. Prior to testing on the optical bench, the photochromic test samples were exposed to 365 nanometer ultraviolet light for about 15 minutes to activate the photochromic compounds and then placed into a 76° C. oven for about 15 minutes to bleach or inactivate the photochromic compounds. The test samples were then cooled to room temperature, exposed to fluorescent room lighting for at least 2 hours and then kept covered for at least 2 hours prior to testing on an optical bench maintained at 75° F. (23.9° C.). The bench was fitted with a 150 watt Xenon arc lamp, a remote controlled shutter, a copper sulfate bath acting as a heat sink for the arc lamp, a Schott WG-320 nm cut-off filter which removes short wavelength radiation, a neutral density filter(s) and a sample holder in which the sample to be tested was inserted. A collimated beam of light from a tungsten lamp was passed through the sample at a small angle normal to the surface of the sample. After passing through the test sample, the light from the tungsten lamp was directed through a photopic filter attached to a detector. The photopic filter passes wavelengths such that the detector mimics the response of the human eye. The output signals from the detector(s) were processed by a radiometer.

Change in optical density ($\Delta$OD) was determined by inserting a photochromic test sample in the bleached state into the sample holder, adjusting the transmittance scale to 100%, opening the shutter from the Xenon lamp to provide ultraviolet radiation to change the sample from the bleached state to an activated (i.e., darkened) state, measuring the transmittance in the activated state, and calculating the change in optical density according to the formula $\Delta OD = \log(100/\% Ta)$ where % Ta is the percent transmittance in the activated state and the logarithm is to the base 10.

The $\Delta$ OD/Min, which represents the sensitivity of the photochromic compound's response to UV light, was measured over the first five (5) seconds of UV exposure, then expressed on a per minute basis. The saturation optical density (OD) was taken under identical conditions as the $\Delta$ AD/Min, except UV exposure was continued for 15 minutes. The lambda max of Band A and Band B reported in Table 1 are two wavelengths in the visible spectrum at which the maximum absorption of the activated (colored) form of the photochromic compound in ethyl cellulose resin occurs. In most cases but not all, the lambda max at Band A is greater than the lambda max at Band B. Side fused is the side of the benzopyran to which the heterocyclic ring is fused. The Bleach Rate T ½ is the time interval in seconds for the absorbance of the activated form of the benzopyran in the test polymer to reach one half the highest absorbance at room temperature (72° F., 22.2° C.) after removal of the source of activating light, Results are tabulated in Table 1.

TABLE 1

| | | Ethyl Cellulose Resin Samples | | | | |
|---|---|---|---|---|---|---|
| Example Number | Side Fused | Lambda Max | | Sensitivity $\Delta$OD | $\Delta$OD @ SAT | Bleach Rate T 1/2 (Sec.) |
| | | Band A | Band B | | | |
| 1 | h | 443 | 530 | 0.03 | 0.20 | >800 |
| 2 | h | 409 | 536 | — | — | — |
| 3 | f | 459 | 530 | 0.47 | 0.54 | 630 |
| 4 | f | 467 | 539 | 0.14 | 0.07 | 119 |
| 5 | f | 467 | 520 | 0.15 | 0.13 | 405 |
| 6 | g | 460 | 527 | 0.40 | 0.56 | 548 |
| 7 | g | 460 | 509 | 0.08 | 0.05 | 101 |
| 8 | g | 460 | 517 | 0.16 | 0.33 | 489 |
| 9 | f | 431 | 587 | 0.04 | 0.03 | 463 |
| 10 | f | 454 | 624 | 0.06 | 0.15 | >600 |
| 11 | f | 477 | 570 | 0.05 | 0.11 | 576 |
| 12 | f | 468 | 546 | 0.10 | 0.16 | 472 |

TABLE 1-continued

| Example Number | Side Fused | Ethyl Cellulose Resin Samples | | | | |
|---|---|---|---|---|---|---|
| | | Lambda Max | | Sensitivity | ΔOD | Bleach Rate |
| | | Band A | Band B | ΔOD | @ SAT | T 1/2 (Sec.) |
| 13 | h | 418 | 530 | 0.05 | 0.21 | >800 |
| 14 | h | 461 | 550 | 0.15 | 0.51 | >800 |
| 15 | h | 461 | 537 | 0.54 | 1.35 | >1200 |
| 16 | h | 462 | 550 | 0.33 | 0.32 | 598 |
| 17 | h | 460 | 526 | 0.13 | 0.13 | 496 |
| 18 | h | 466 | 556 | 0.26 | 0.31 | 727 |
| 19 | h | 456 | 524 | 0.67 | 1.57 | >800 |
| 20 | h | 462 | 535 | 0.53 | 1.15 | >1200 |
| 21 | h | 462 | 534 | 0.49 | 0.81 | >1200 |
| CE | f | 430 | 522 | 0.42 | 0.18 | 85 |

CE represents Comparative Example.

The results in Table 1 for benzopyrans prepared from different hydroxydibenzofurans, i.e., hydroxydibenzofurans having hydroxy substituents at positions 1, 2, 3 or 4, such as in Examples 2, CE, 9 and 13, respectively, demonstrate that different results are obtained for benzopyrans prepared from each different hydroxydibenzofuran. The Examples having ortho substitution on at least one of the 3,3-diphenyl groups, such as Examples 1, 3, 5, 6, 8, 10, 11, 12, 14, 15, 19, 20, and 21, have higher results for each test parameter than corresponding compounds lacking an ortho substituent, such as Examples 2, 4, 7, 9, 13, and 18. In a comparison of Example 14 and 15, which are both ortho substituted but X is sulfur in Example 15, Example 15 revealed higher results for sensitivity, Δ AD at saturation, and bleach rate. Similar findings were obtained in a comparison of Example 16 and 17, which are not ortho substituted but X is sulfur in Example 16. Example 16 revealed higher results for sensitivity, Δ AD at saturation, and bleach rate. Also, the bleach rates for most of the Examples with the h side fused are as long or longer than the results for the other examples.

Although the present invention has been described with reference to the specific details of particular embodiments thereof, it is not intended that such details be regarded as limitations upon the scope of the invention except insofar as to the extent that they are included in the accompanying claims.

I claim:

1. A benzopyran compound represented by the following graphic formula:

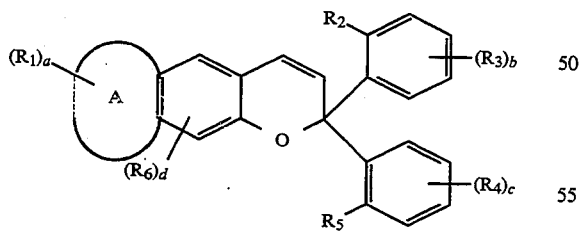

wherein, (a) A is a substituted or unsubstituted heterocyclic ring selected from the group consisting of benzothieno and benzofurano, the 2,3 position or 3,2 position of said heterocyclic ring being fused to the f, g, or h side of said benzopyran compound, each $R_1$ is $C_1$-$C_{10}$ alkyl, $C_5$-$C_7$ cycloalkyl, $C_1$-$C_5$ alkylcarbonyl, $C_1$-$C_5$ alkoxycarbonyl, halo($C_1$-$C_5$alkyl-carbonyl, $C_1$-$C_5$ monoalkylaminocarbonyl, formyl, hydroxy, halogen, R(R')N—, the group —O—L, or is a substituted or unsubstituted benzo fused to the benzo portion of the benzothieno or benzofurano group, said benzo substituents being $C_1$-$C_4$ alkyl, $C_1$-$C_4$ alkoxy, halogen, $C_5$-$C_7$ cycloalkyl, or $C_1$-$C_4$ alkyl substituted $C_5$-$C_7$ cycloalkyl, R is a $C_1$-$C_3$ alkyl, R' is hydrogen or a $C_1$-$C_3$ alkyl, L is $C_1$-$C_{10}$ alkyl, phenyl($C_1$-$C_3$)alkyl, $C_1$-$C_5$ alkylcarbonyl, ($C_1$-$C_5$)alkoxycarbonyl, halo($C_1$-$C_5$)alkyl-carbonyl, $C_1$-$C_5$ monoalkylaminocarbonyl, acrylyl, methacrylyl, acetonyl, pyridyl, substituted or unsubstituted arylcarbonyl, said aryl of the arylcarbonyl group being phenyl or naphthyl, said aryl substituents being the same as said benzo substituents, and said halogen (or halo) groups being chloro, fluoro, or bromo;

(b) $R_2$ and $R_5$ are each hydrogen, $C_1$-$C_5$ alkyl, $C_1$-$C_5$ alkoxy, fluoro, or chloro; each $R_3$ and each $R_4$ are hydroxy, $C_1$-$C_{10}$ alkyl, $C_1$-$C_{10}$ alkoxy, $C_5$-$C_7$ cycloalkyl, halogen, R(R')N—, or the group, —O—L', said L' is phenyl($C_1$-$C_3$)alkyl, acrylyl, or methacrylyl; $R_6$ is $C_1$-$C_{10}$ alkyl, $C_5$-$C_7$ cycloalkyl, $C_1$-$C_5$ alkylcarbonyl, $C_1$-$C_5$ alkoxycarbonyl, halo($C_1$-$C_5$alkylcarbonyl, $C_1$-$C_5$ monoalkylaminocarbonyl, formyl, hydroxy, halogen, cyano, R(R')N—, or the group, —O—L, said halogen or halo substituents being chloro, fluoro or bromo; and a and d are each the integer 0 or 1, b and c are each the integers 0, 1, or 2, provided that when $R_2$ and $R_5$ are each hydrogen and b and c are each the integer 0, A is fused to the g or h side of said benzopyran compound, and provided further that at least one of $R_2$ and $R_5$ is other than hydrogen when A is fused to the f side of said benzopyran compound.

2. The benzopyran compound of claim 1 wherein:

(a) A is a benzothieno or benzofurano group represented by the following graphic formula:

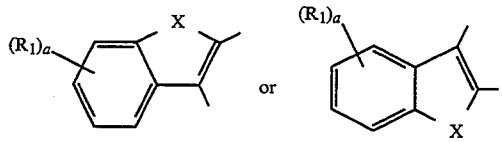

wherein X is oxygen or sulfur; $R_1$ is a $C_1$-$C_3$ alkyl, $C_5$-$C_6$ cycloalkyl, $C_1$-$C_3$ alkylcarbonyl, $C_1$-$C_3$ alkoxycarbonyl, halo($C_1$-$C_2$)alkylcarbonyl, $C_1$-$C_3$ alkylaminocarbonyl, formyl, chloro, fluoro, R(R')N—, the group, —O—L, or is a substituted or unsubstituted benzo fused to the benzo portion of the benzothieno or benzofurano group, said benzo substituents being $C_1$-$C_3$ alkyl, $C_1$-$C_3$ alkoxy, halogen, $C_5$-$C_6$ cycloalkyl, R is a $C_1$-$C_2$ alkyl, R' is hydrogen or a $C_1$-$C_2$ alkyl, L is a $C_1$-$C_5$ alkyl, phenyl($C_1$-$C_2$)alkyl, $C_1$-$C_2$ alkylcarbonyl, $C_1$-$C_2$ alkoxycarbonyl, halo($C_1$-$C_2$)alkylcarbonyl, $C_1$-$C_2$ monoalkylaminocarbonyl, acrylyl, or methacrylyl, said halo or halogen substituent being chloro or fluoro; and (b) $R_2$ and $R_5$ are each hydrogen, $C_1$-$C_3$ alkyl, $C_1$-$C_3$ alkoxy, or fluoro; $R_3$ and each $R_4$ are $C_1$-$C_5$ alkyl, $C_1$-$C_5$ alkoxy, $C_5$-$C_6$ cycloalkyl, fluoro, R(R')N—, or the group, —O—L', wherein R is a $C_1$-$C_2$ alkyl, R' is hydrogen or a $C_1$-$C_2$ alkyl, L' is $C_1$-$C_5$ alkyl, phenyl($C_1$-$C_2$)alkyl, acrylyl, or methacrylyl; $R_6$ is formyl, $C_1$-$C_3$ alkyl, $C_5$-$C_6$ cycloalkyl, $C_1$-$C_3$ alkylcarbonyl, $C_1$-$C_3$ alkoxycarbonyl, halo($C_1$-$C_3$)alkylcarbonyl, $C_1$-$C_3$ monoalkylaminocarbonyl, fluoro, R(R')N—, or the group, —O—L, said halo substituent being chloro or fluoro; a, b, and d are each the integers 0 or 1, and c is the integer 0, 1, or 2.

3. The benzopyran compound of claim 2 wherein $R_1$ is a methyl, methoxy, formyl, benzo, methoxycarbonyl, or methylamino-carbonyl; $R_2$ is hydrogen; $R_3$, $R_4$, and $R_5$ are each methyl, methoxy, or fluoro; $R_6$ is methyl, methoxy, formyl, methoxycarbonyl, or methylaminocarbonyl; and a, b, c, and d are each the integers 0 or 1.

4. A benzopyran compound selected from the group consisting of:
   (a) 3-(2,4-dimethoxyphenyl), 3-(4-methoxyphenyl)-(3H)-benzo(b)furo[2,3-f]-1-benzopyran;
   (b) 3-(2,4-dimethoxyphenyl), 3-(4-methoxyphenyl)-8-methoxy-(3H)-naphtho[1,2-b]furo [2,3-f]-1 -benzopyran;
   (c) 2-(2,4-dimethoxyphenyl), 2-(4-methoxyphenyl)-(2H)-benzo(b)thieno[3,2-h]-1-benzopyran;
   (d) 2-(2,4-dimethoxyphenyl), 5,8-dimethyl, 2-(4-methoxyphenyl)-(2H)-benzo(b)thieno[3,2-h]-1-benzopyran;
   (e) 2-(2,4-dimethoxyphenyl), 2-(4-methoxyphenyl)-(2H)-benzo(b)furo[2,3-h]-1-benzopyran;
   (f) 2-(2,4-dimethoxyphenyl), 2-(4-methoxyphenyl)-(2H)-benzo(b)furo[3,2-h]-1-benzopyran;
   (g) 2,2-bis (4-methoxyphenyl)-(2H)-benzo(b)thieno[3,2-h]-1-benzopyran;
   (h) 2-(2-fluoro, 4,5-dimethoxyphenyl), 2-(4-methoxyphenyl)-(2H)-benzo(b)thieno[3,2-h]-1-benzopyran;
   (i) 3-(2,4-dimethoxyphenyl), 3-(4-methoxyphenyl)-(2H)-benzo(b)furo[2,3-f]-1-benzopyran; and
   (j) 3-(2,4-dimethoxyphenyl), 3-(2-fluorophenyl)-(3H)-benzo(b)thieno[2,3-f]-1 -benzopyran.

5. A photochromic article comprising an organic host material and a photochromic amount of at least one photochromic benzopyran compound of claim 1.

6. The photochromic article of claim 5 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethane, poly(ethylene terephthalate), polystyrene, copoly(styrene-methylmethacrylate), copoly(styreneacrylonitrile), polyvinylbutyral and polymers of members of the group consisting of polyol(allyl carbonate) monomers, polyfunctional acrylate monomers, and diallylidene pentaerythritol monomers.

7. The photochromic article of claim 6 wherein the benzopyran is selected from the photochromic benzopyran compounds of claim 2.

8. The photochromic article of claim 7 wherein the benzopyran is selected from photochromic benzopyran compounds of claim 3.

9. The photochromic article of claim 8 wherein the organic host material is a solid transparent homopolymer or copolymer of diethylene glycol bis(allyl carbonate), polycarbonate, poly(methylmethacrylate), polyvinylbutyral or a polyurethane.

10. The photochromic article of claim 9 wherein the photochromic compound is present in an amount of from about 0.15 to 0.35 milligrams per square centimeter of organic host material surface to which the photochromic substance(s) is incorporated or applied.

11. The photochromic article of claim 10 wherein the article is a lens.

12. A photochromic article comprising, in combination, a solid transparent polymerized organic host material and a photochromic amount of
   (a) at least one organic photochromic compound having at least one activated absorption maxima within the visible range of between about 400 and 700 nanometers associated with said host material, and
   (b) at least one photochromic benzopyran compound of claim 1.

13. The photochromic article of claim 12 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethane, poly(ethylene terephthalate), polystyrene, copoly(styrene-methylmethacrylate), copoly(styreneacrylonitrile), polyvinylbutyral and polymers of members selected from the group consisting of polyol(allyl carbonate) monomers, polyfunctional acrylate monomers, and diallylidene pentaerythritol monomers.

14. The photochromic article of claim 13 wherein the photochromic benzopyran compound (b) is selected from the naphthopyran compounds of claim 2.

15. The photochromic article of claim 14 wherein the organic host material is a solid transparent homopolymer or copolymer of diethylene glycol bis(allyl carbonate), polycarbonate, poly(methylmethacrylate), polyvinylbutyral, or a polyurethane.

16. The photochromic article of claim 15 wherein the organic photochromic compound (a) is selected from the group consisting of spiro(indoline)naphthoxazines, spiro(indoline)pyridobenzoxazines, spiro(benzindoline)pyridobenzoxazines, spiro(benzindoline)naphthoxazines, spiro(benzindoline)naphthopyrans, spiro(indoline)benzoxazines, spiro(indoline)benzopyrans, spiro(indoline)naphthopyrans, spiro(indoline)quinopyrans, spiro(indoline)pyrans, 3H-naphtho[2,1-b]-pyrans, 2H-naphtho[1,2-b]pyrans, and mixtures of such photochromic substances.

17. The photochromic article of claim 16 wherein each photochromic compound associated with the organic host material is present in an amount of from about 0.15 to 0.35 milligrams per square centimeter of organic host material surface to which the photochromic compound is incorporated or applied.

18. The photochromic article of claim 17 wherein the article is an ophthalmic lens.

19. A photochromic article comprising, in combination, a solid transparent polymerized organic host material and a photochromic amount of (a) at least one organic photochromic compound represented by the graphic formula:

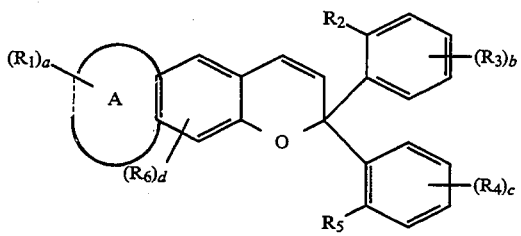

wherein A is a substituted or unsubstituted heterocyclic ring selected from the group consisting of benzothieno and benzofurano, the 2,3 position or 3,2 position of said heterocyclic ring being fused to the f, g, or h side of said benzopyran compound, each $R_1$ is $C_1$-$C_3$ alkyl, $C_1$-$C_3$ alkoxycarbonyl, $C_1$-$C_3$ monoalkylaminocarbonyl, formyl, the group, —O—L, or is a substituted or unsubstituted benzo ring fused to the benzo portion of the benzothieno or benzofurano group, said benzo substituents being $C_1$-$C_3$ alkyl, $C_1$-$C_3$ alkoxy, or fluoro, L is a $C_1$-$C_3$ alkyl; $R_2$ and $R_5$ are each hydrogen, $C_1$-$C_3$ alkyl, $C_1$-$C_3$ alkoxy or fluoro; each $R_3$ and each $R_4$ are $C_1$-$C_3$ alkyl, $C_1$-$C_3$ alkoxy or fluoro; $R_6$ is $C_1$-$C_3$ alkyl, $C_1$-$C_3$ alkoxycarbonyl, $C_1$-$C_3$ monoalkylaminocarbonyl or formyl; and a and d are each the integer 0 or 1, b and c are each the integers 0, 1, or 2, provided that when $R_2$ and $R_5$ are each hydrogen and b and c are each the integer 0, A is fused to the g or h side of said benzopyran compound, and provided further that at least one of $R_2$ $R_5$ is other than hydrogen when A is fused to the f side of said benzopyran compound; and (b) at least one organic photochromic compound selected from the group consisting of spiro(indoline)naphthoxazines, spiro(indoline)pyrido-benzoxazines, spiro(indoline)benzoxazines, spiro(indoline)-benzopyrans, spiro(indoline)naphthopyrans, 3H-naphtho[2,1-b]pyrans, and 2-H-naphtho[1,2-b]pyrans, the weight ratio of the photochromic compounds (a):(b) being from about 1:3 to about 3:1.

20. The photochromic article of claim 19 wherein the organic host material is a solid transparent homopolymer or copolymer of diethylene glycol bis(allyl carbonate), polycarbonate, poly(methylmethacrylate), polyvinylbutyral, or a polyurethane.

21. The photochromic article of claim 20 wherein $R_1$ is a methyl, methoxy, formyl, benzo, methoxycarbonyl, or methylaminocarbonyl; $R_2$ is hydrogen; $R_3$, $R_4$ and $R_5$ are each methyl, methoxy, or fluoro; $R_6$ is methyl, methoxy, formyl, methoxycarbonyl, or methylaminocarbonyl; and a, b and d are each the integers 0 or 1, and c is the integer 0, 1, or 2.

22. The photochromic article of claim 21 wherein the organic photochromic compound (b) is selected from spiro(indolino)naphthoxazine or spiro(indoline)-pyridobenzoxazines.

* * * * *